United States Patent
Wang et al.

(10) Patent No.: US 7,771,745 B2
(45) Date of Patent: Aug. 10, 2010

(54) FAST DISSOLVING TABLET AND METHOD OF PREPARING THE SAME

(75) Inventors: Wen-Che Wang, Danshuei Township, Taipei County (TW); Hui-Yu Chen, Banciao (TW); Chih-Chiang Yang, Taipei (TW)

(73) Assignee: Pharmaceutical Industry Technology and Development Center, Taipei Hsien (TW)

( * ) Notice: Subject to any disclaimer, the term of this patent is extended or adjusted under 35 U.S.C. 154(b) by 1577 days.

(21) Appl. No.: 10/836,331

(22) Filed: May 3, 2004

(65) Prior Publication Data

US 2005/0196438 A1    Sep. 8, 2005

(30) Foreign Application Priority Data

Mar. 8, 2004   (TW) .............................. 93106010 A

(51) Int. Cl.
*A61K 9/20*   (2006.01)
*A61K 9/26*   (2006.01)
*A61K 9/46*   (2006.01)

(52) U.S. Cl. ...................... 424/466; 424/464; 424/469; 424/470

(58) Field of Classification Search ................... 424/464
See application file for complete search history.

(56) References Cited

U.S. PATENT DOCUMENTS

2003/0180352 A1 *   9/2003   Patel et al. .................. 424/465
2003/0206959 A9 *  11/2003   Kipp et al. .................. 424/489

OTHER PUBLICATIONS

Remington, et al, "The Science and Practice of Pharmacy" 19th Ed., vol. II, 1995 Mack Publishing, Chap. 92, pp. 1615 et seq.*
Sugimoto, et al, "The Preparation of Rapidly Disintegrating Tablets in the Mouth," Pharmaceutical Development and Technology (2001), 6(4):487-493.*
Itiola and Pilpel, "Tableting Characteristics of Metronidazole Formulations," International Journal of Pharmaceutics (1986), 31:99-105.*
Sugimoto, et al., Pharmaceutical Development and Technology, 64(4), 487-493 (2001).*

* cited by examiner

*Primary Examiner*—S. Tran
(74) *Attorney, Agent, or Firm*—Occhiuti Rohlicek & Tsao LLP

(57) ABSTRACT

The present invention provides a method for making a fast dissolving tablet. The method includes the steps of (a) preparing a first solution containing a hydrophilic polymer and a starch; (b) preparing a second solution containing a pharmaceutically active ingredient and a surfactant; (c) blending the first and the second solution together to form a plurality of granule powders by granulation; (d) mixing the granule powders with excipients; and (e) applying a compression-molding process to form the fast dissolving tablet.

18 Claims, 2 Drawing Sheets

FAST DISSOLVING TABLET AND METHOD OF PREPARING THE SAME

RELATED INVENTION

The present invention claims the priority of Taiwan Application No. 93106010, filed on Mar. 8, 2004, which is herein incorporated by reference.

BACKGROUND OF THE INVENTION

1. Field of the Invention

The present invention relates to a pharmaceutical composition, and more specifically to a fast dissolving tablet and method of preparing the same.

2. Description of the Related Art

There are various types of oral administrative medicines, such as, tablets, capsules, granules, powders, syrups and the like. Orally administrated medicines, however, suffer from many drawbacks. Tablets and capsules, for example, may be difficult to swallow for the elderly or children. Granules and powders, may leave an unpleasant taste after dosage or possibly enter the respiratory tract or lungs, additionally, dosage of syrups, may be difficult measured, particularly for the elderly or children.

Therefore, many researches regarding fast dissolving tablets has been undertaken recently to provide a new generation rapidly dissolved and safely swallowed tablets, and their dose can be accurately measured. The tablets must additionally possess adequate hardness to facilitate the packaging process.

Several related arts are disclosed as follows. Japanese Patent No. 76420/1977 and 24410/1983 describe a method of preparing a porous tablet which comprises blending a tablet-constituting composition with inert solvent, solidification, compressing the resulting solid into tablets, and evaporating solvent by freeze-drying. U.S. Pat. No. 5,501,861 discloses a method of preparing a fast dissolving tablet comprising a water-soluble saccharide (such as sugar, starch, lactose, sugar alcohol, or tetrose) and a pharmacologically active ingredient, which comprises compressing the blended solid into tablets with molding pressure of 5~130 kg/cm$^2$ and evaporating solvent by freeze-drying.

The above fast dissolving tablets are prepared by Zydis freeze-drying (from R. P. Scherer, England). This method, however, suffer from high process cost and insufficient mechanical strength of the preparation.

Japanese Patent No. 15830/1986 describes a method of preparing a porous tablet which comprises blending a pharmaceutically active ingredient with an antacid having a porous and extra fine crystal structure. The composition described in this patent is prepared by heating and melting the ingredients, so that it is inferior in the scope of compatible medicament and disintegrating ability of the preparation in an oral cavity.

European Patent No. 0914818 discloses a fast dissolving tablet comprising sugar alcohol or saccharide, a disintegrant, and a pharmaceutically active ingredient. The hardness of the tablet, however, is only 3 NT, and does not satisfy generally packaging requirements.

Therefore, it is necessary to develop a preparation which offers acceptable disintegration speed in an oral cavity and possesses a sufficient mechanical strength so as to protect the preparation from destruction in the course of manufacture.

SUMMARY OF THE INVENTION

In order to solve the conventional problems, an object of the invention is to provide a fast dissolving tablet having rapid disintegration rate, sufficient hardness to resist destruction in the course of manufacture and storage, and low cost.

To achieve the above objects, the invention provides a fast dissolving tablet comprising a pharmaceutically active ingredient, a starch, a hydrophilic polymer, a surfactant, and an excipient.

The tablet provided in the invention may be rapidly dissolved in an oral cavity, due to the hydrophilic polymer having strong water absorption, so that it can be advantageously used for treatment of diseases in the elderly or children. Additionally, the dissolution rate of tablets is improved by the surfactant in an oral cavity, particularly for very slightly dissolved drugs.

Another object of the invention is to provide a method for preparing a fast dissolving tablet, comprising the following steps. A first solution comprising a hydrophilic polymer and a starch is provided. A second solution comprising a pharmaceutical active ingredient and a surfactant is then provided. Subsequently, the first and second solutions are blended to form granule powders by granulating. Finally, granule powders and excipients are blended, and a compression-molding process is performed.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

Figure 1:
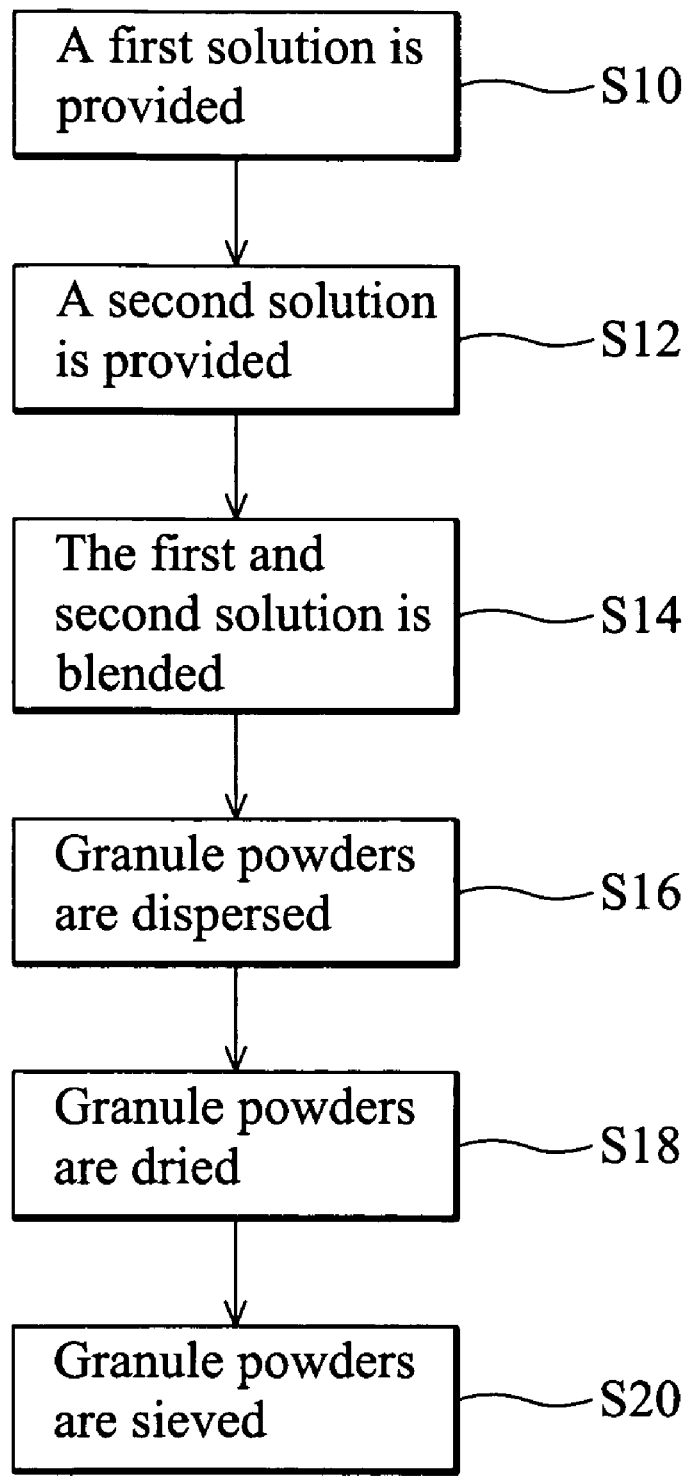
FIG. 1 is a flow chart of the granulating of the invention.

FIG. 1 illustrates the method of preparing the fast dissolving tablet according to the embodiment of the invention. First, referring to FIG. 1, a first solution is provided in step S10. The first solution comprises solute comprising a hydrophilic polymer and a starch and solvent comprising water or ethanol, wherein the hydrophilic polymer comprises PEG, PVP, carbopol, polysaccharide, agar, MC, or HPMC, and the starch preferably comprises potato starch. The first solution is powdery.

Subsequently, a second solution is provided in step S12. The second solution comprises solute comprising a pharmaceutically active ingredient and a surfactant and solvent comprising water or ethanol, wherein the pharmaceutically active ingredient comprises any optional orally administered drugs, and the surfactant comprises edible surfactants comprising phospholipid.

The pharmaceutically active ingredient may be one member at least selected from the group: (1) vitamins, for example, vitamin A, vitamin D, vitamin E, vitamin $B_1$, vitamin $B_2$, vitamin $B_6$, vitamin $B_{12}$, or vitamin C, minerals, for example, Ca, Mg, Fe, or protein, and amino acid or oligosaccharide and the like.

(2) antipyretic-analgesic-antiinflammatory agents, for example, aspirin, acetaminophen, ethenzamide, ibuprofen, diphenhydramine hydrochloride, dl-chorpheniramine maleate, dihydrocodeine phosphate, noscapine, methylephedrine hydrochloride, phenylpropanolamine hydrochloride, caffeine, serratiopeptidase, lysozyme chloride, tolfenamic acid, mefenamic acid, diclofenac sodium, flufenamic acid, salicylamide, aminopyrine, ketoprofen, indomethacin, bucolome, or pentazocine and the like.

(3) antipsychotic drugs, for example, chlorpromazine, reserpine, chlordiazepoxide, diazepam, imipramine, maprotiline, amphetamine, estazolam, nitrazepam, diazepam, phenobarbital sodium, scopolamine hydrobromide, diphenhydramine hydrochloride, or papaverine hydrochloride and the like.

(4) gastrointestinal function conditioning agents, for example, diastase, saccharated pepsin, scopolia extract, lipase AP, cinnamon oil, berberine chloride, resistant lactic acid bacterium, lactobacillus bifidus, magnesium carbonate, sodium hydrogen carbonate, magnesium aluminometasilicate, synthetic hydrotalcite, precipitated calcium carbonate, or magnesium oxide and the like.

(5) antitussive-expectorants, for example, chloperastine hydrochloride, dextromethorphan hydrobromide, theophylline, potassium guaiacolsulfonate, guaifenesin, oxytetracycline, triamcinolone acetonide, chlorhexidine hydrochloride, or lidocaine and the like.

(6) antihistamines, for example, diphenhydramine hydrochloride, promethazine, isothipendyl hydrochloride, or dl-chlorpheniramine maleate and the like.

(7) cardiotonics, for example, etilefrine hydrochloride, procainamide hydrochloride, propranolol hydrochloride, pindolol, isosorbide, furosemide, delapril hydrochloride, captopril, hexamethonium bromide, hydralazine hydrochloride, labetalol hydrochloride, or methyldopa and the like.

(8) vasoconstrictors, for example, phenylephrine hydrochloride, carbocromen hydrochloride, molsidomine, verapamil hydrochloride, cinnarizine, dehydrocholic acid, or trepibutone and the like.

(9) antibiotics, for example, cephems, penems, carbapenems, cefalexin, amoxicillin, pivmecillinam hydrochloride, or cefotiam dihydrochloride and the like.

(10) chemotherapeutic drugs, for example, sulfamethizole or thiazosulfone and the like.

(11) antidiabetic agents, for example, tolbutamide or voglibose and the like.

(12) drugs for osteoporosis, for example, ipriflavone and the like.

(13) skeletal muscle relaxants, for example, methocarvamol and the like.

Subsequently, the first and second solutions are blended in step S14 to form granule powders by granulating. The formed granule powders are then uniformly dispersed in step S16 simultaneously. Granule powders are then dried in step S18. Finally, the granule powders are sieved in step S20. The granulating comprises wet granulating, dry granulating, spray granulating, and fluidized bed granulating.

Figure 2:
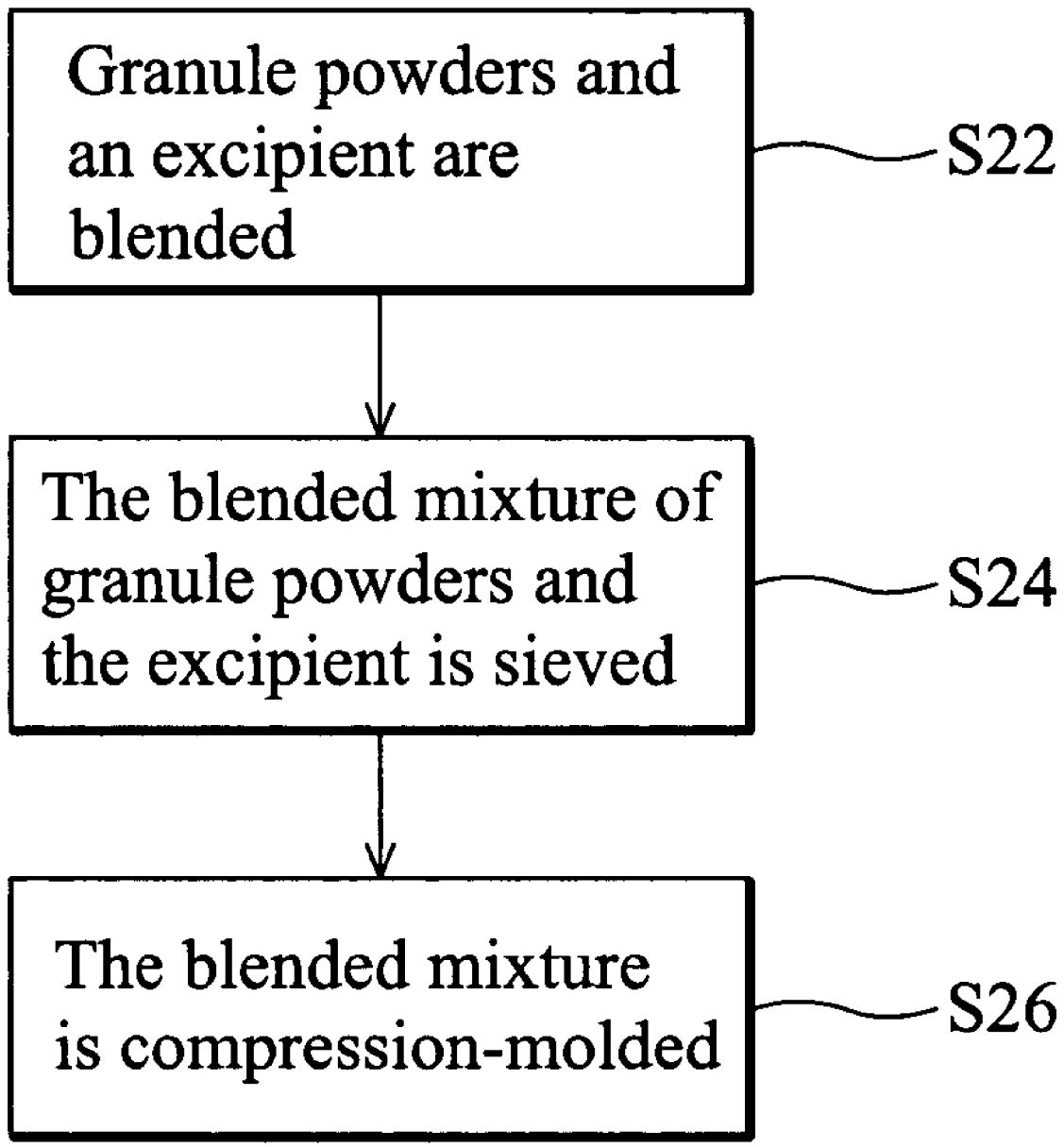
FIG. 2 is a flow chart of the compression-molding of the invention.

Next, referring to FIG. 2, granule powders and excipients are blended in step S22. The excipients comprise disintegrating agents, effervescent agents, sweeteners, and lubricants comprising saccharide, alcohol, and sugar alcohol, wherein saccharide comprises monosaccharide or disaccharide, and sugar alcohol comprises mannitol, sorbitol, xylitol, or glycerol.

Subsequently, the mixture of granule powders and the excipients is sieved in step S24. After sieving, the mixture is compression-molded in step S26 with a tabletting machine, for example, a High-Speed Rotary Tabletting Machine.

The molding pressure of the High-Speed Rotary Tabletting Machine is about 800~1200 lb/cm$^2$, preferably 1000 lb/cm$^2$. The molding speed thereof is about 15~20 rpm, preferably 16 rpm.

The fast dissolving tablet of the invention comprises a pharmaceutically active ingredient in a proportion of generally about 5~45% by weight, a starch in a proportion of generally about 20~30% by weight, a hydrophilic polymer in a proportion of generally about 2~10% by weight, a surfactant in a proportion of generally about 2~10% by weight, and a excipient in a proportion of generally about 40~50% by weight. Additionally, the porosity of the tablet is about 30~70%, the disintegration time (the time required for complete dissolution by saliva in an oral cavity in a healthy adult male) thereof is less than 1 min, the hardness thereof is about 20~60 NT, and the brittleness thereof is less than 2%.

EXAMPLE 1

A first solution comprising a PEG6000 (hydrophilic polymer), a lecithin (surfactant), a potato starch, and ethanol was prepared as the following steps. First, 50 g of PEG6000 and 10 g of lecithin were added into 350 ml of ethanol, and stirred. Next, 50 g of potato starch was added into the blended solution. Finally, the powdery first solution was formed.

Subsequently, a second solution comprising acetaminophen (antipyretic-analgesic-antiinflammatory agents), lecithin (surfactant), and H$_2$O was prepared as described in the following step. 400 g of acetaminophen and 50 g of lecithin were added into 160 ml of H$_2$O, and stirred.

Next, a wet granulating process was performed as follows. The first and second solutions were blended to form granule powders. Subsequently, granule powders were dried in a dryer at 45° C., and then sifted through a sieve with 400 μm diameter mesh.

Next, granule powders and excipients were blended with a V-shaped blender. The excipient comprised 250 g of lactose (disaccharide), 100 g of mannitol (sugar alcohol), and 100 g of crospovidone (disintegrating agents). Subsequently, the blend was sifted through a sieve with 200 μm diameter mesh. Finally, 400 g of blend was compression-molded to form a tablet with a High-Speed Rotary Tabletting Machine. The molding pressure was about 1000 lb/cm$^2$, and the molding speed was about 15.9 rpm.

In this example, 400 g of acetaminophen in a proportion is generally about 40% by weight, 50 g of potato starch in a proportion is generally about 5% by weight, 50 g of PEG6000 in a proportion is generally about 5% by weight, 50 g of lecithin in a proportion is generally about 5% by weight, and 450 g of excipient comprising 250 g of lactose, 100 g of mannitol, and 100 g of crospovidone in a proportion is generally about 25% by weight.

EXAMPLE 2

A first solution comprising a PEG6000 (hydrophilic polymer), a lecithin (surfactant), a potato starch, and ethanol was prepared as described in the following steps. First, 50 g of PEG6000 and 10 g of lecithin were added into 350 ml of ethanol, and stirred. Next, 50 g of potato starch was added into the blended solution. Finally, the powdery first solution was formed.

Subsequently, a second solution comprising nifedipine (antipyretic-analgesic-antiinflammatory agents), lecithin (surfactant), and H$_2$O was prepared as the following step. 5 g of nifedipine and 50 g of lecithin were added into 160 ml of H$_2$O, and stirred.

Next, a wet granulating process was performed as follows. The first and second solutions were blended to form granule powders. Subsequently, granule powders were dried in a dryer at 45° C., and then granule powders were sifted through a sieve with 400 μm diameter mesh.

Next, granule powders and excipients were blended with a V-shaped blender. The excipients comprised 250 g of lactose (disaccharide), 100 g of mannitol (sugar alcohol), and 100 g of crospovidone (disintegrating agents). Subsequently, the blend was sifted through a sieve with 200 μm diameter mesh. Finally, 400 g of blend was compression-molded to form a tablet with a High-Speed Rotary Tabletting Machine. The molding pressure was about 1000 lb/cm$^2$, the molding speed was about 15.9 rpm.

In this example, 5 g of nifedipine in a proportion is generally about 5% by weight, 50 g of potato starch in a proportion is generally about 5% by weight, 50 g of PEG6000 in a proportion is generally about 5% by weight, 50 g of lecithin in a proportion is generally about 5% by weight, and 450 g of excipient comprising 250 g of lactose, 100 g of mannitol, and 100 g of crospovidone in a proportion is generally about 25% by weight.

EXAMPLE 3

A first solution comprising a PEG6000 (hydrophilic polymer), a lecithin (surfactant), a potato starch, and ethanol was prepared as the following steps. First, 50 g of PEG600.0 and 10 g of lecithin were added into 350 ml of ethanol, and stirred. Next, 50 g of potato starch was added into the blended solution. Finally, the powdery first solution was formed.

Subsequently, a second solution comprising famotidine (antipyretic-analgesic-antiinflammatory agents), lecithin (surfactant), and H$_2$O was prepared as the following step. 20 g of famotidine and 50 g of lecithin were added into 160 ml of H$_2$O, and stirred.

Next, a wet granulating process was performed as follows. The first and second solutions were blended to form granule powders. Subsequently, granule powders were dried in a dryer at 45° C., and then granule powders were sifted through a sieve with 400 μm diameter mesh.

Next, granule powders and excipients were blended with a V-shaped blender. The excipients comprised 250 g of lactose (disaccharide), 100 g of mannitol (sugar alcohol), and 100 g of crospovidone (disintegrating agents). Subsequently, the blend was sifted through a sieve with 200 μm diameter mesh. Finally, 400 g of blend was compression-molded to form a tablet with a High-Speed Rotary Tabletting Machine. The molding pressure was about 1000 b/cm$^2$, the molding speed was about 15.9 rpm.

In this example, 20 g of famotidine in a proportion is generally about 40% by weight, 50 g of potato starch in a proportion is generally about 5% by weight, 50 g of PEG6000 in a proportion is generally about 5% by weight, 50 g of lecithin in a proportion is generally about 5% by weight, and 450 g of excipient comprising 250 g of lactose, 100 g of mannitol, and 100 g of crospovidone in a proportion is generally about 25% by weight.

EXAMPLE 4

A first solution comprising a PEG6000 (hydrophilic polymer), a lecithin (surfactant), a potato starch, and ethanol was prepared as described in the following steps. First, 50 g of PEG6000 and 10 g of lecithin were added into 350 ml of ethanol, and stirred. Next, 50 g of potato starch was added into the blended solution. Finally, the powdery first solution was formed.

Subsequently, a second solution comprising Al(OH)$_3$ (gastrointestinal function conditioning agents), lecithin (surfactant), and H$_2$O was prepared as described in the following step. 400 g of Al(OH)$_3$ and 50 g of lecithin were added into 160 ml of H$_2$O, and stirred.

Next, a wet granulating process was performed as follows. The first and second solution was blended to form granule powders. Subsequently, granule powders were dried in a dryer at 45° C., and then granule powders were sifted through a sieve with 400 μm diameter mesh.

Next, granule powders and excipients were blended with a V-shaped blender. The excipients comprised 250 g of lactose (disaccharide), 100 g of mannitol (sugar alcohol), and 100 g of crospovidone (disintegrating agents). Subsequently, the blend was sifted through a sieve with 200 μm diameter mesh. Finally, 400 g of blend was compression-molded to form a tablet with a High-Speed Rotary Tabletting Machine. The molding pressure was about 1000 lb/cm$^2$, the molding speed was about 15.9 rpm.

In this example, 400 g of Al(OH)$_3$ in a proportion is generally about 40% by weight, 50 g of potato starch in a proportion is generally about 5% by weight, 50 g of PEG6000 in a proportion is generally about 5% by weight, 50 g of lecithin in a proportion is generally about 5% by weight, and 450 g of excipient comprising 250 g of lactose, 100 g of mannitol, and 100 g of crospovidone in a proportion is generally about 25% by weight.

EXAMPLE 5

To illustrate the effects of the invention in further detail, the following characteristics of the tablets prepared in the foregoing examples were determined, comprising disintegration time, hardness, and brittleness. The results are shown in Table 1.

(1) Disintegration Time

The disintegration time of each tablet was determined in accordance with the disintegration test as described in the following. First, 37±2° C., proper amount of water used as solvent was added into the container of the test machine (PHARMA TEST PTZ1 E type). Next, six tablets were added into the container, and the container was covered by a plastic cover. Subsequently, the test machine shook the container until the tablets were disintegrated completely. The mean of the results of six determinations of each pharmaceutically active ingredient was adopted respectively.

(2) Hardness

The hardness of each tablet was determined in accordance with the hardness test as described in the following. First, six tablets were placed on the hardness tester (SHIN KWANG SK-32060 type). Next, pressure was applied from the long axis until the tablets were cracked. The mean of results of six determinations of each pharmaceutically active ingredient was adopted respectively.

(3) Brittleness

The brittleness of each tablet was determined in accordance with the brittleness test described as follows. First, 6~6.5 g of sixteen tablets (380~420 mg/per tablet) were placed on the sieve (10 mesh). After dropped powders were removed, the precise sample weight (As) was measured. The sample was then added into the test machine (PHARMA TEST PTFE type), and the test machine was spun at a speed of 25 rpm for 100 turns. After the sample was taken out, all dropped powders were removed again. Finally, the precise sample weight ($A_0$) was measured. As a result, Brittleness=($A_0/As$)*100. The mean of the results of sixteen determinations of each pharmaceutically active ingredient was adopted respectively.

TABLE 1

| Pharmaceutically active ingredient | Disintegration time(sec) | Hardness (NT) | brittleness (%) |
|---|---|---|---|
| acetaminophen | 22 ± 3 | 35.4 ± 5.3 | 1.2 |
| nifedipine | 53 ± 2 | 46.9 ± 4.8 | 0.2 |
| famotidine | 32 ± 2 | 24.2 ± 1.4 | 1.3 |
| Al(OH)$_3$ | 25 ± 3 | 27.9 ± 2.3 | — |

The results of Table 1 indicate that the disintegration time of the fast dissolving tablets of the present invention is less than 1 min, and the brittleness thereof is less than 2%. Therefore, the elderly, children, or those with impaired swallowing ability are able to swallow the tablets, due to rapid disintegration and absorption in an oral cavity. Additionally, an adequate mechanical strength of 20~50NT is obtained, facilitating the packaging process in production lines.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method for preparing a fast dissolving tablet, comprising:
    preparing a powdery first solution which comprises a hydrophilic polymer and a starch;
    preparing a second solution which comprises a pharmaceutically active ingredient and a surfactant;
    blending the first and second solutions to form a plurality of granule powders by a granulating process;
    mixing the granule powders with at least an excipient; and
    applying a compression-molding process to form the fast dissolving tablet; wherein the compression-molding process applies a pressure of about 800~1200 lb/cm$^2$, wherein the tablet has a porosity of about 30~70%, and wherein the tablet has a disintegration time of less than 1 minute.

2. The method as claimed in claim 1, wherein the hydrophilic polymer comprises PEG, PVP, carbopol, polysaccharide, agar, MC, or HPMC.

3. The method as claimed in claim 1, wherein the surfactant comprises edible surfactant.

4. The method as claimed in claim 1, wherein the surfactant comprises lecithin.

5. The method as claimed in claim 1, wherein the solvent used in the first solution and second solution is $H_2O$ or ethanol.

6. The method as claimed in claim 1, wherein the granulating process comprises dry granulation, wet granulation, fluidized bed granulation, or spray granulation.

7. The method as claimed in claim 1, wherein the diameter of the granule powders is about 300~500 μm.

8. The method as claimed in claim 1, wherein the excipient is a disintegrating agent, an effervescent, a lubricant, or a sweetener.

9. The method as claimed in claim 1, wherein the excipient comprises a saccharide, an alcohol, or a sugar alcohol.

10. The method as claimed in claim 9, wherein the saccharide is a monosaccharide or a disaccharide.

11. The method as claimed in claim 9, wherein the sugar alcohol is mannitol, sorbitol, xylitol, or glycerol.

12. The method as claimed in claim 1, wherein the compression-molding process uses a speed of about 15~20 rpm.

13. The method as claimed in claim 1, wherein the pharmaceutically active ingredient is 5~45% by weight of the fast dissolving tablet.

14. The method as claimed in claim 1, wherein the starch is 20~30% by weight of the fast dissolving tablet.

15. The method as claimed in claim 1, wherein the hydrophilic polymer is 2~10% by weight of the fast dissolving tablet.

16. The method as claimed in claim 1, wherein the surfactant is 2~10% by weight of the fast dissolving tablet.

17. The method as claimed in claim 1, wherein the excipient is 40~50% by weight of the fast dissolving tablet.

18. The method as claimed in claim 8, wherein the lubricant is 1~3% by weight of the fast dissolving tablet.

* * * * *

UNITED STATES PATENT AND TRADEMARK OFFICE
CERTIFICATE OF CORRECTION

PATENT NO. : 7,771,745 B2  Page 1 of 1
APPLICATION NO. : 10/836331
DATED : August 10, 2010
INVENTOR(S) : Wen-Che Wang et al.

It is certified that error appears in the above-identified patent and that said Letters Patent is hereby corrected as shown below:

Title Page, Please correct item (73) Assignee to read "Medical and Pharmaceutical Industry Technology and Development Center"

Signed and Sealed this

Twenty-third Day of November, 2010

David J. Kappos
*Director of the United States Patent and Trademark Office*